US00PP25718P3

(12) United States Plant Patent
Grazzini

(10) Patent No.: US PP25,718 P3
(45) Date of Patent: Jul. 14, 2015

(54) *ANGELONIA* PLANT NAMED 'G2X-11996-2'

(50) Latin Name: *Angelonia angustifolia*
Varietal Denomination: G2X-11996-2

(71) Applicant: GARDEN GENETICS LLC, Bellefonte, PA (US)

(72) Inventor: Richard A. Grazzini, Bellefonte, PA (US)

(73) Assignee: Garden Genetics LLC, Bellefonte, PA (US)

( * ) Notice: Subject to any disclaimer, the term of this patent is extended or adjusted under 35 U.S.C. 154(b) by 188 days.

(21) Appl. No.: 13/987,043

(22) Filed: Jun. 27, 2013

(65) Prior Publication Data
US 2015/0020275 P1 Jan. 15, 2015

(51) Int. Cl.
*A01H 5/00* (2006.01)

(52) U.S. Cl.
USPC ..... Plt./404

(58) Field of Classification Search
USPC ..... Plt./404
See application file for complete search history.

*Primary Examiner* — Annette Para
(74) *Attorney, Agent, or Firm* — Jondle & Associates, P.C.

(57) ABSTRACT

A new and distinct variety of *Angelonia* plant named 'G2X-11996-2' particularly characterized by an upright, dense basal-branching plant habit and having clear, pink flower color is disclosed.

3 Drawing Sheets

Genus and species: *Angelonia angustifolia.*
Variety denomination: 'G2X-11996-2'.

BACKGROUND OF THE NEW PLANT

The present invention comprises a new and distinct variety of *Angelonia* plant, botanically known as *Angelonia angustifolia* and hereinafter referred to by the variety name 'G2X-11996-2'. The new variety originated from a cross conducted in July 2010 in Bellefonte, Pa. between the female parent *Angelonia* plant 'C282-1' (unpatented) and the male parent *Angelonia* plant 'Anwhitim' (U.S. Plant Pat. No. 19,866). A single plant selection was subsequently chosen for further evaluation and asexual propagation.

'G2X-11996-2' was first propagated via vegetative cuttings and via aseptic in vitro tissue culture in October 2011 in Bellefonte, Pa. and has been asexually reproduced by vegetative cuttings in Bellefonte, Pa. for approximately 5 generations. Concurrently, 'G2X-11996-2' has been propagated via aseptic in vitro tissue culture and subculture since October 2011. 'G2X-11996-2' has been found to retain its distinctive characteristics through successive asexual propagations via vegetative cuttings and in vitro tissue culture.

Plant Breeder's Rights for this variety have not been applied for. 'G2X-11996-2' has not been sold or made publicly available anywhere in the world more than one year prior to the filing date of this application.

SUMMARY OF THE INVENTION

The following are the most outstanding and distinguishing characteristic of this new variety when grown under normal horticultural practices in a greenhouse in Bellefonte, Pa.

1. Upright, dense basal-branching habit; and
2. Clear, pink flower color.

DESCRIPTION OF THE PHOTOGRAPHS

This new *Angelonia* plant is illustrated by the accompanying photographs; the colors shown are as true as can be reasonably obtained by conventional photographic procedures. The photographs are of a whole plant about 19 weeks old.

DESCRIPTION OF THE NEW VARIETY

Figure 1:
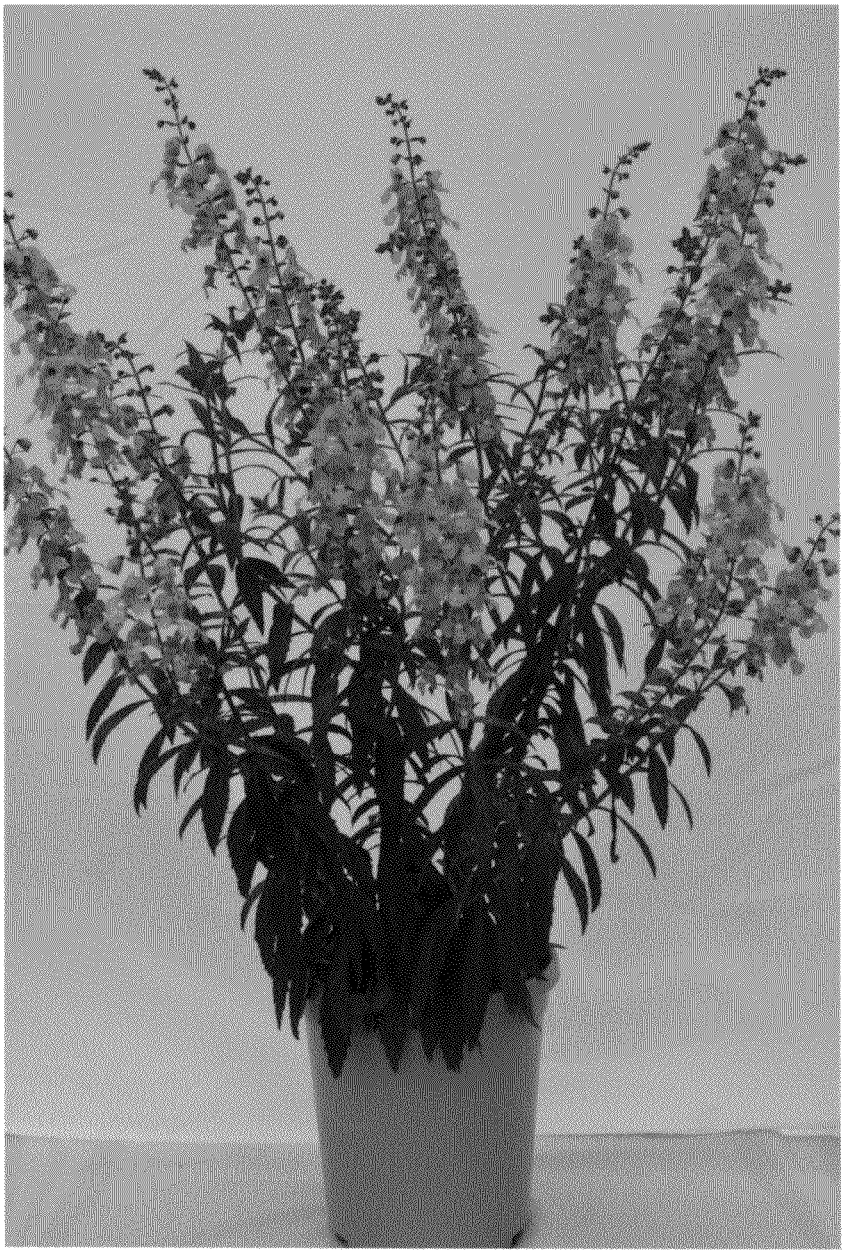
FIG. 1 shows a whole plant of 'G2X-11996-2' in a trade 1-gallon pot.
Figure 2:
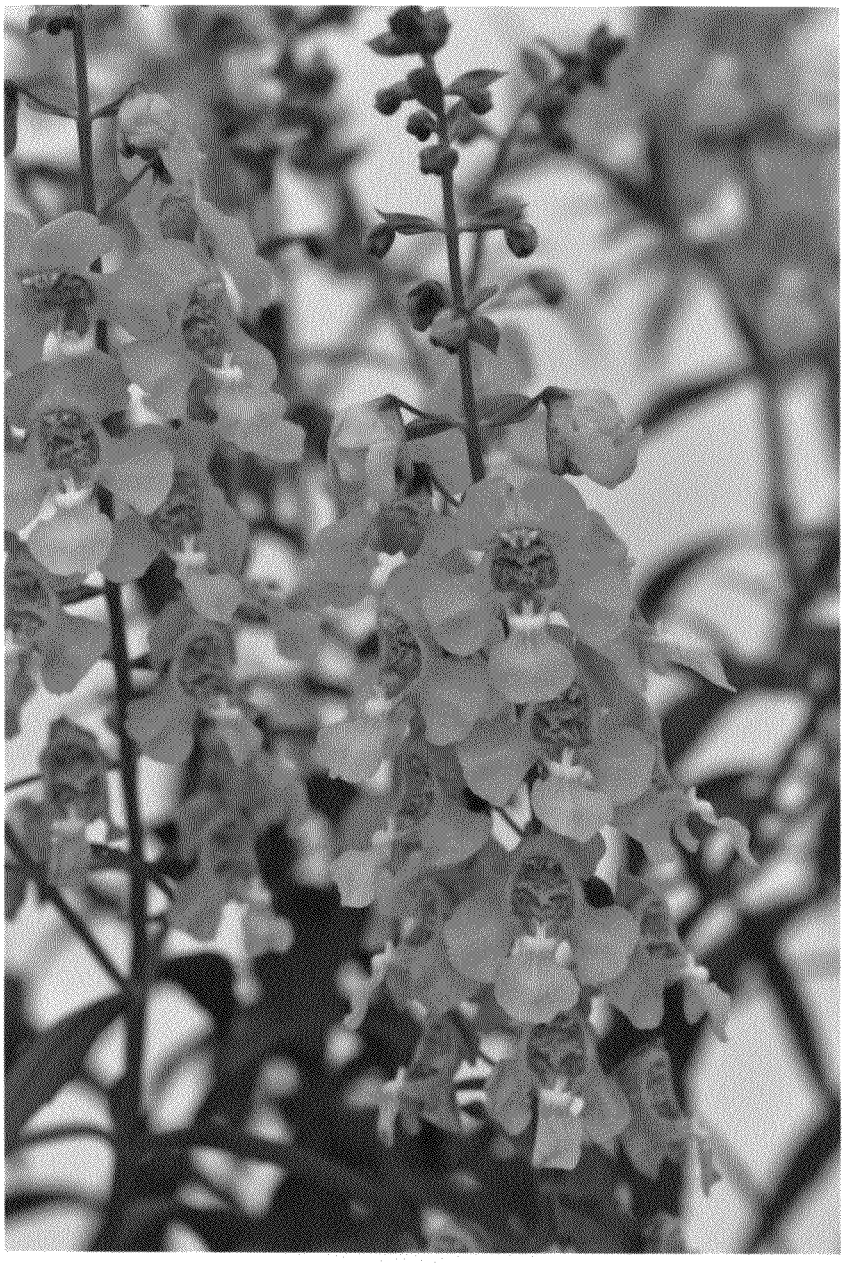
FIG. 2 shows a close-up of an inflorescence of 'G2X-11996-2'.
Figure 3:
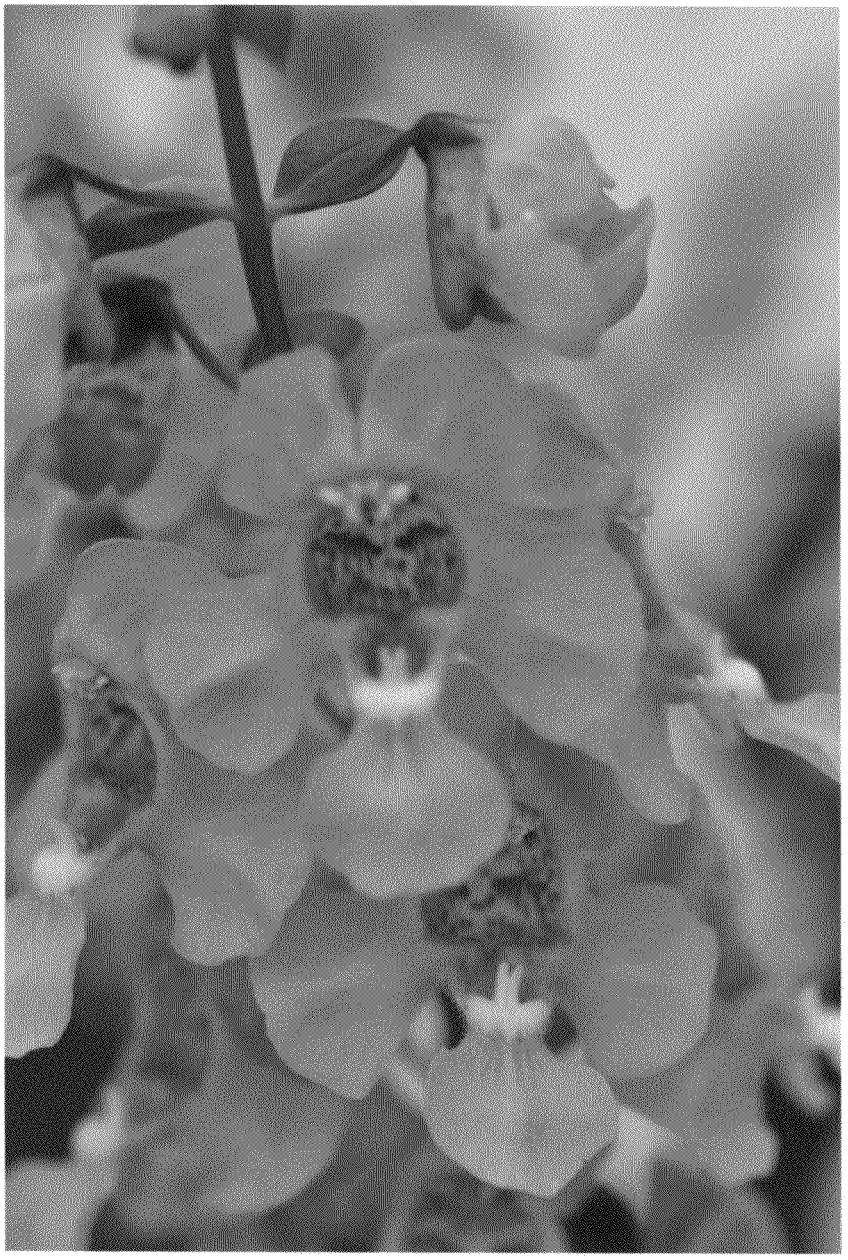
FIG. 3 shows a close-up of an individual floret of 'G2X-11996-2'.

The following detailed description sets forth the distinctive characteristics of *Angelonia angustifolia* 'G2X-11996-2'. The data which define these characteristics was collected from asexual reproductions carried out in Bellefonte, Pa. The plant history was taken on June 7 of 2013 on 18 week old plants grown in 1-gallon pots. The plants were grown from vegetatively propagated cuttings from mother stock grown in a controlled climate greenhouse with natural light. Color readings were taken under natural light in the greenhouse. Color references are primarily to the Panton color chart, #747XR second printing (1987-1988 edition).

DETAILED BOTANICAL DESCRIPTION OF THE NEW PLANT

Classification:
- *Family.*—Plantaginaceae.
- *Botanical.*—*Angelonia angustifolia.*
- *Common.*—*Angelonia.*

Parentage:
- *Female parent.*—'C282-1' (unpatented).
- *Male parent.*—'Anwhitim' (U.S. Plant Pat. No. 19,866).

Plant:
- *Form.*—1-gallon, mature, flowering.
- *Growth and branching habit.*—Upright, dense basal-branching.

*Height*.—56.0 cm.
*Width*.—41.0 cm.
*Time to produce a finished flowering plant*.—8 to 10 weeks from unrooted cuttings.
*Lastingness of individual blooms on the plant*.—>5 days.
*Outdoor plant performance*.—Good to very good; good heat tolerance.
*Time to initiate roots*.—7 to 10 days.
*Root description*.—White, abundant.

Leaves:
*Arrangement*.—Opposite, whorls alternate.
*Length*.—10.0 cm.
*Width*.—2.2 cm.
*Shape*.—Long and narrow, rhombic.
*Apex*.—To a sharp point, acuminate.
*Base*.—Margin attached at base, cuneate.
*Margin*.—Serrate from 50% of the length to the tip.
*Color*.—Dark green upper, mid green lower. Upper surface: Pantone 5743C. Lower surface: Pantone 574C.
*Texture* (*for each surface*).—Glossy (upper), Glossy (lower).
*Venation pattern*.—Parallel to margin, penni-parallel.
*Venation color*.—Pantone 5743C.

Stem:
*Length* (*first stem*).—25.0 cm to 36.0 cm.
*Diameter* (*just below first branch*).—0.6 cm.
*Internodes length*.—3.0 cm.
*Color*.—Pantone 575C (mid green).
*Texture*.—Smooth.
*Anthocyanin*.—Absent.
*Pedicel*.—Color: Pantone 575C. Length: 1.4 cm. Diameter: ca. 1.0 mm. Texture: Smooth.
*Note*.—Each pedicel has a small "leaf" at its base. This pedicel-leaf is the same color as the upper surface of the stem-leaf, Pantone 5743C.

Bud:
*Shape*.—Globular to ovate.
*Diameter*.—2.0 mm to 5.0 mm.
*Length*.—2.0 mm to 5.0 mm.
*Color at tight bud*.—Pantone 575C.

Flower:
*Blooming habit*.—Annual.
*Floret and inflorescence type*.—Single flower, branched inflorescence.
*Color*.—Clear pink, dark spots within throat, white spot on lower lip. Upper surface: Pantone 244C. Lower surface: Pantone 244C. Color of spot within throat: Pantone 255C.
*Florets per raceme*.—>40.
*Floret diameter*.—ca. 2.5 cm.
*Petal*.—Quantity per flower: 5 (fused). Apex: Smooth. Margin: Smooth. Texture: Smooth. Size: Upper lip: Length: 1.0 cm. Width: 0.8 cm. Lower lip, lateral petal: Length: 0.9 cm. Width: 0.9 cm. Lower lip, central petal: Length: 1.5 cm. Width: 0.9 cm.
*Sepals*.—Quantity: 5. Color: Pantone 574C. Length: 2.5 mm. Width: 1.0 mm. Shape: Blunt, coming to a point. Apex: Pointed. Base: Attached. Margin: Smooth.
*Sepal anthocyanin*.—None.
*Sepal texture*.—Smooth.
*Fragrance*.—None.

Reproductive organs:
Stamens.—4.
*Filament color*.—Light green.
*Pollen amount*.—Abundant.
*Pollen color*.—White to creamy-yellow.
*Pistil*.—1.
*Stigma*.—Entire, not split.
*Style color*.—Light green.

Fruit and seed set: G2X-11996-2 is fertile and produces moderate amounts of seed. Seed shape and size is typical of tetraploid *Angelonia*.

Disease and insect/pest resistance: Typical of species.

COMPARISON WITH PARENTAL AND COMMERCIAL VARIETIES

*Angelonia* 'G2X-11996-2' differs from the female parent *Angelonia* plant 'C282-1' (unpatented) in that 'G2X-11996-2' has clear, pink flowers and a large, flat floret display, whereas 'C282-1' has lavender-pink flowers with a small to medium and slightly cupped floret. Additionally, 'G2X-11996-2' is taller than 'C282-1'.

*Angelonia* 'G2X-11996-2' differs from the male parent *Angelonia* plant 'Anwhitim' (U.S. Plant Pat. No. 19,866) in that 'G2X-119966-2' has clear, pink flowers, whereas 'Anwhitim' has white flowers. Additionally, 'G2X-11996-2' has a smaller floret size and shorter, more compact, more densely basal-branched habit than 'Anwhitim'.

*Angelonia* 'G2X-11996-2' differs from the commercial variety *Angelonia angustifolia* 'Balarcink' (U.S. Plant Pat. No. 23,521) in that 'G2X-11996-2' is a taller and broader plant with larger and broader leaves than 'Balarcink'. Also, 'G2X-11996-2' has bright, clear pink-flowers, whereas 'Balarcink' has lavender-pink flowers. Additionally, 'G2X-11996-2' has lighter green leaves and less serrated leaves than 'Balarcink'.

I claim:

1. A new and distinct variety of *Angelonia* plant named 'G2X-11996-2' as described and shown herein.

* * * * *